United States Patent [19]

Sciarra et al.

[11] Patent Number: 4,494,553
[45] Date of Patent: Jan. 22, 1985

[54] VITAL SIGNS MONITOR

[75] Inventors: Michael J. Sciarra, Southampton; Victor L. Cestaro, Farmingville, both of N.Y.

[73] Assignee: F. William Carr, Houston, Tex.

[21] Appl. No.: 250,068

[22] Filed: Apr. 1, 1981

[51] Int. Cl.³ .............................................. A61B 5/08
[52] U.S. Cl. .................................. 128/721; 128/671
[58] Field of Search ............... 128/1.5, 631, 653, 671, 128/694, 698, 715, 721, 903, 774; 73/779; 324/71.1, 207–209, 243

[56] References Cited

U.S. PATENT DOCUMENTS

| | | | |
|---|---|---|---|
| 3,731,184 | 1/1973 | Goldberg et al. | 73/779 X |
| 3,768,459 | 10/1973 | Cannon et al. | 128/775 |
| 3,827,291 | 8/1974 | McCalvey | 73/779 |
| 4,051,522 | 9/1977 | Healy et al. | 128/903 |
| 4,129,125 | 12/1978 | Lester et al. | 128/671 |
| 4,197,856 | 4/1980 | Northrop | 128/721 |
| 4,248,241 | 2/1981 | Tacchi | 128/671 |
| 4,306,567 | 12/1981 | Krasner | 128/721 |
| 4,308,872 | 1/1982 | Watson et al. | 128/721 |
| 4,456,015 | 6/1984 | Sackner | 128/774 X |

OTHER PUBLICATIONS

Slemon, G. R., "Magnetoelectric Devices", Wiley & Sons, N.Y., 1966, pp. 37–39.
Beerwinkle, K. R. et al., "A Low Power Combination Electrocardiogram-Respiration Telemetry Transmitter", *IEEE Transactions on Biomedical Engineering*, (Nov. 1976), pp. 484–486.
Milledge, J. S. and Stott, F. D., "Inductive Plethysmography-A New Respiratory Transducer", *Proceedings of the Physiological Society*, (Jan. 1977), D.3.
Sullivan, M. J. and Kertesz, A., "Signal Detection Via Phase-Locked Sampling in a Magnetic Search Coil Eye Movement Monitor, *IEEE Transactions on Biolmedical Engineering*, (Jan. 1979), pp. 50–56.
FYI: Spotlight on apnea monitoring, *Perinatology-Neonatology*, May/Jun. 1981, pp. 61–64.
Frost and Sullivan, market survey, excerpts.

*Primary Examiner*—Kyle L. Howell
*Assistant Examiner*—Francis J. Jaworski
*Attorney, Agent, or Firm*—Browning, Bushman, Zamecki & Anderson

[57] ABSTRACT

Provision is made to monitor for vital signs, such as respiratory activity and cardiac activity. The monitoring equipment is mounted by a belt to a person being monitored. Multiple Inductance coils carried by the belt move relative to each other in response to breathing, and the associated mutual inductance changes provide sensory signals to reflect the breathing. Electrical signals indicative of such vital signs are transmitted by radio wave to a central monitor which can monitor the activity of numerous persons. A plurality of such patient units including vital signs sensors and transmitters in combination with a single central monitor may be used to monitor multiple patients. The present invention is useful in monitoring to attempt to prevent sudden infant death syndrome, or crib death, and in intensive care units or cardiac units of hospitals and the like.

28 Claims, 17 Drawing Figures

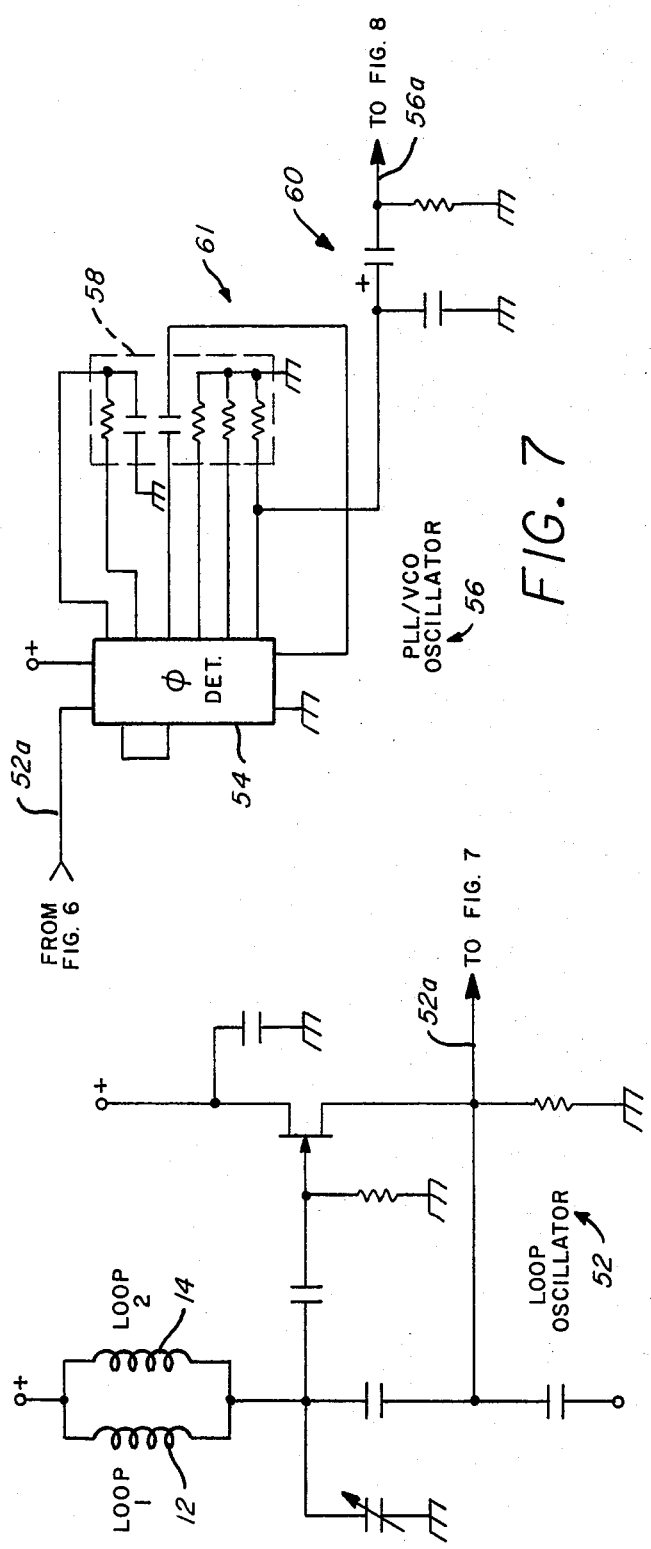
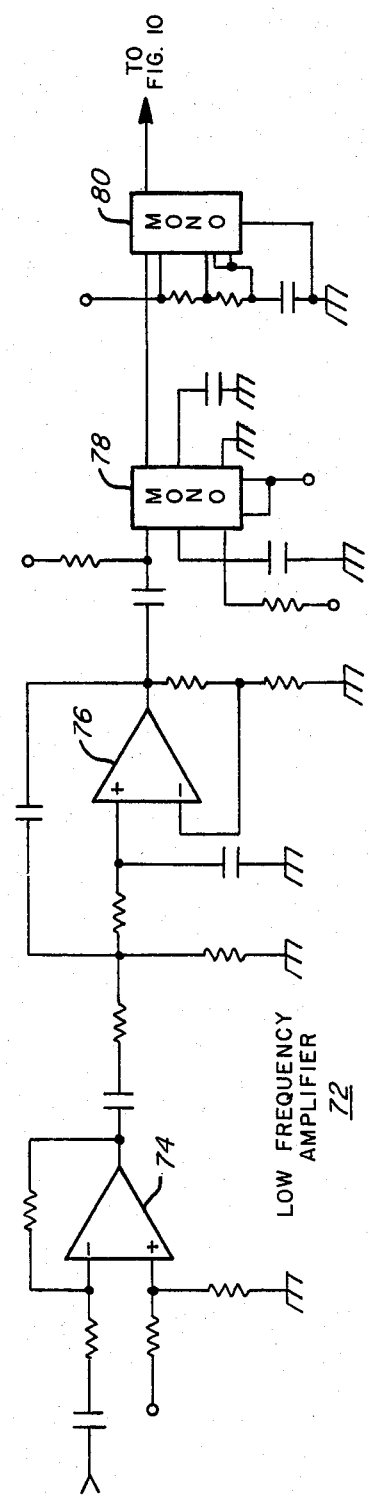
FIG. 7
FIG. 6
FIG. 9

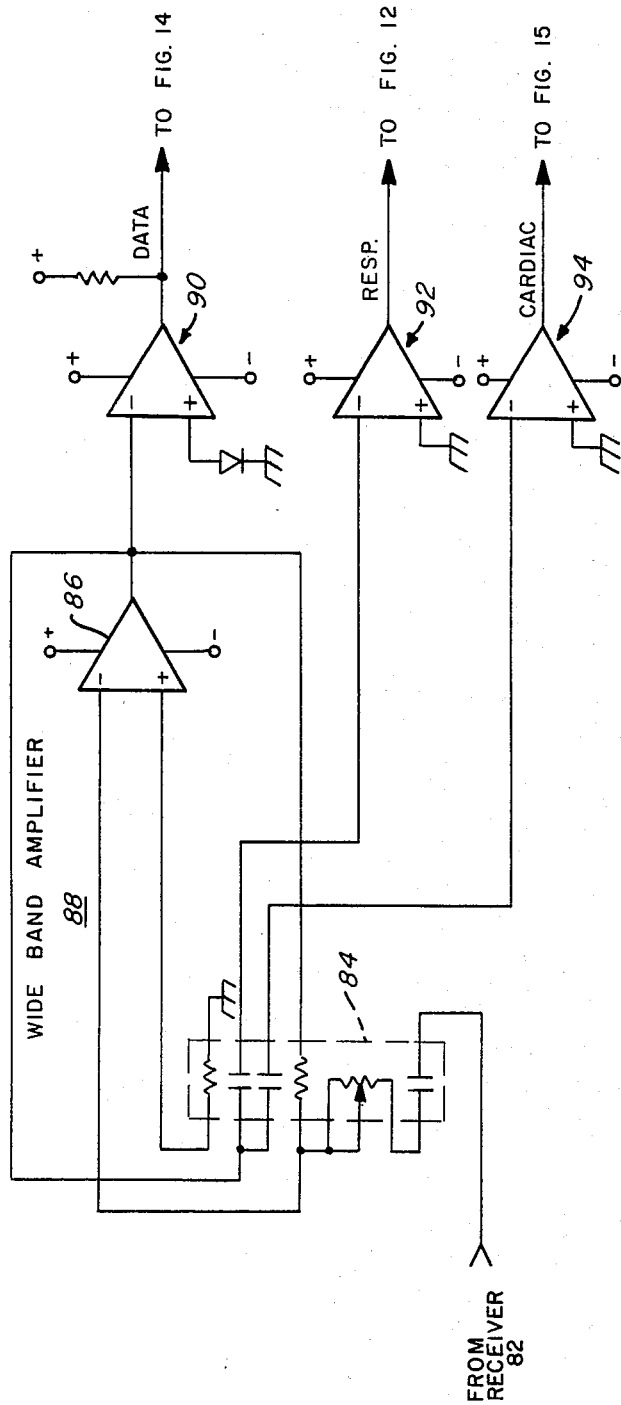
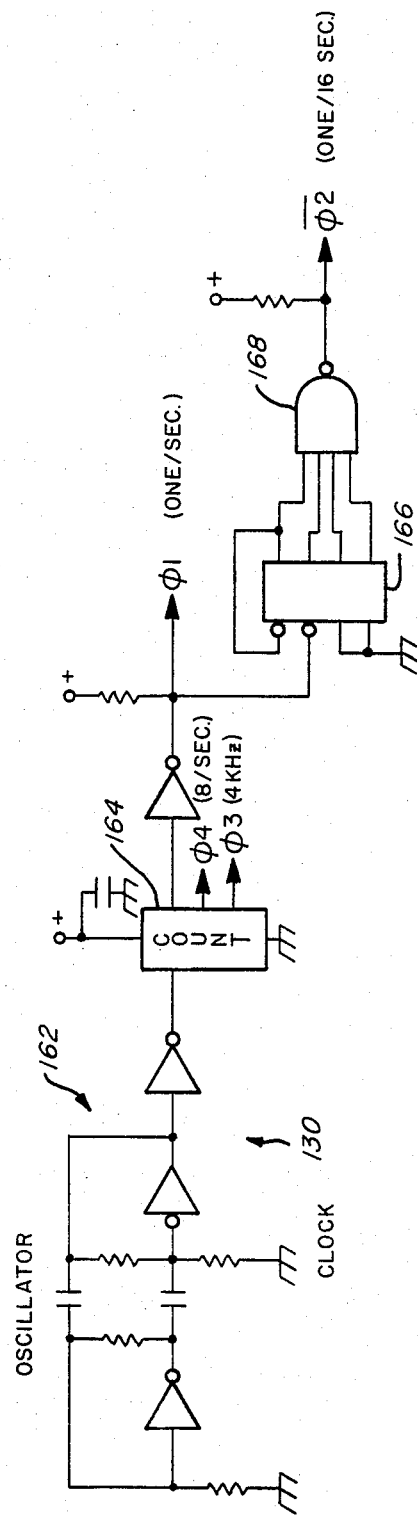
FIG. 11
FIG. 17

VITAL SIGNS MONITOR

FIELD OF THE INVENTION

The present invention relates to electronic systems for monitoring vital signs, such as respiration and cardiac activity.

DESCRIPTION OF PRIOR ART

There have been several types of vital sign monitors to detect interrupted respiration. However, each of these types has suffered from several shortcomings. A first type of monitor was based on detecting the temperature differential between inhaled and exhaled air. Usually, a temperature sensor was mounted near a patient's nose to detect changes in temperature in the air between inhaling and exhaling. However, since a person normally breathes once every five or more seconds, a substantial time delay in seconds lapsed, usually twenty or more, before an abnormal condition was sensed.

Another type of monitor utilized a strain gage sensor whose resistance changed as the patient's chest cavity expanded and contracted during breathing. However, for reference reading purposes, the strain gage was required to be applied to the patient's body in a set or fixed state of tension. Usually the strain gage was contained in a bandage or wrap in some manner about the patient's thorax. If the wrap loosened in any way, however, the readings obtained by the strain gage were no longer accurate.

Another type of sensor was based on actual electrode attachment to the person being monitored. Differences in the galvanic response were measured as the patient's thorax expanded and contracted. However, attachment of the electrodes to the patient was a cumbersome process. Further, the electrodes could become separated from the patient's body.

Still other types of sensors used transducers which attempted to detect respiration by sensing body motion caused by breathing through transducers which sensed movement of the mattress on which the patient was lying. However, the mattresses were also sensitive to other body movements of the patient and other vibrations. Additionally, the mattresses were also subject to physical damage and deterioration.

SUMMARY OF INVENTION

Briefly, the present invention provides a new and improved apparatus and system for monitoring vital signs in one or more patients. Each of the one or more patients to be monitored has a patient unit which includes a transducer in the form of an inductive coil which detects vital signs, such as the patient's breathing, by changing in inductance. The patient unit also includes a mounting means, such as a belt or vest, which mounts the transducer means to the patient's thorax. A transmitter of the patient unit transmits radio signals indicative of the patient's vital signs. Cardiac activity of the patient is also sensed and monitored according to the present invention.

Radio signals indicating the vital signs of each patient being monitored are received at a central unit, where they are processed and displayed. Acceptable limits on the vital signs being monitored are established at the central unit, so that abnormal conditions are rapidly detected and corrective action may then be taken.

BRIEF DESCRIPTION OF THE DRAWINGS

FIGS. 6, 7, 8, 9 and 10 are schematic electrical circuit diagrams of the patient unit of FIGS. 1 and 3; and FIGS. 11, 12, 13, 14, 15, 16 and 17 are schematic electrical circuit diagrams of the central unit of FIG. 2.

DESCRIPTION OF PREFERRED EMBODIMENT

Figure 1:
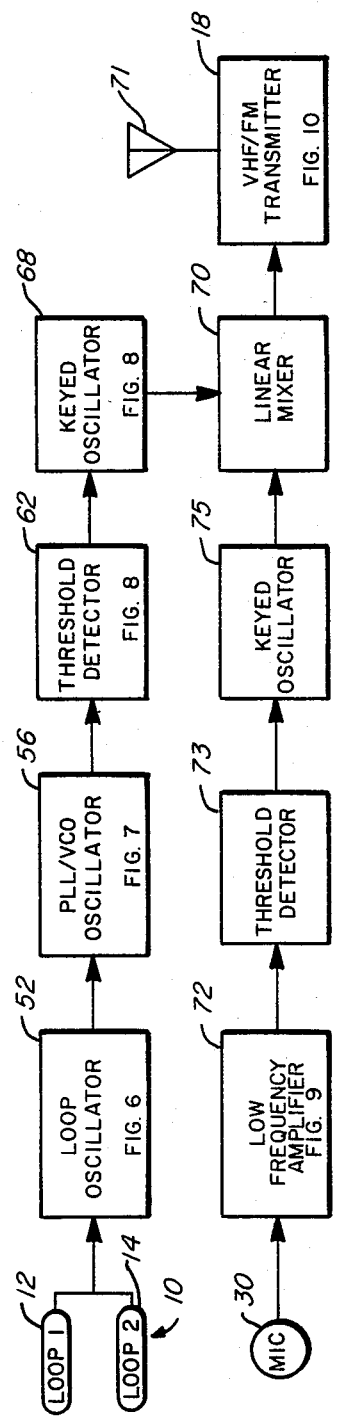
FIG. 1 is a schematic electrical circuit diagram of a patient unit according to the present invention.

In the drawings, a system according to the present invention for monitoring vital signs in one or more patients is set forth. In the system of the present invention, each patient being monitored has associated therewith a patient unit P (FIGS. 1 & 3) for monitoring vital signs in the patient and transmitting radio signals to a central or control monitor unit C (FIG. 2) which monitors the vital signs of the patient and indicates to an observer or attendant any change in the vital signs of the patient so that remedial or corrective action can be taken.

Figure 3:
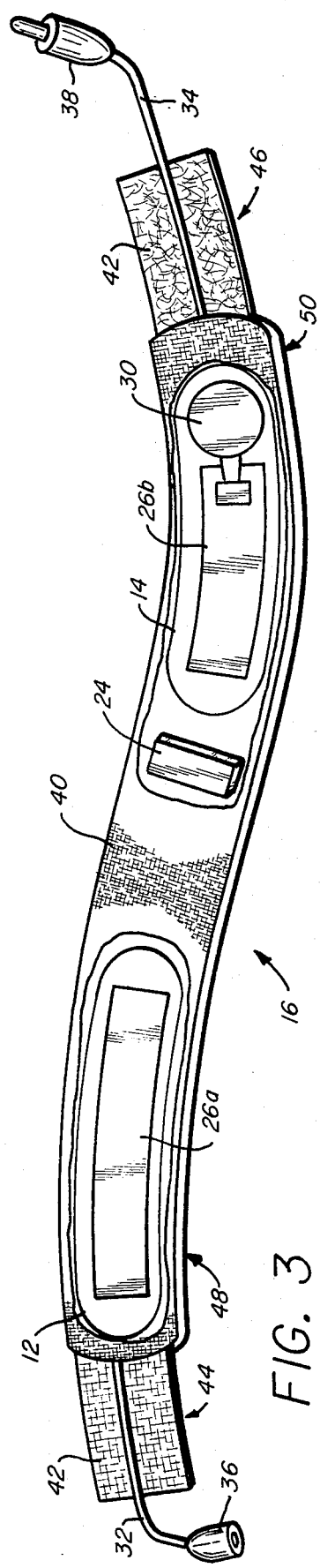
FIG. 3 is an isometric view of a patient unit according to the present invention.
Figure 4:
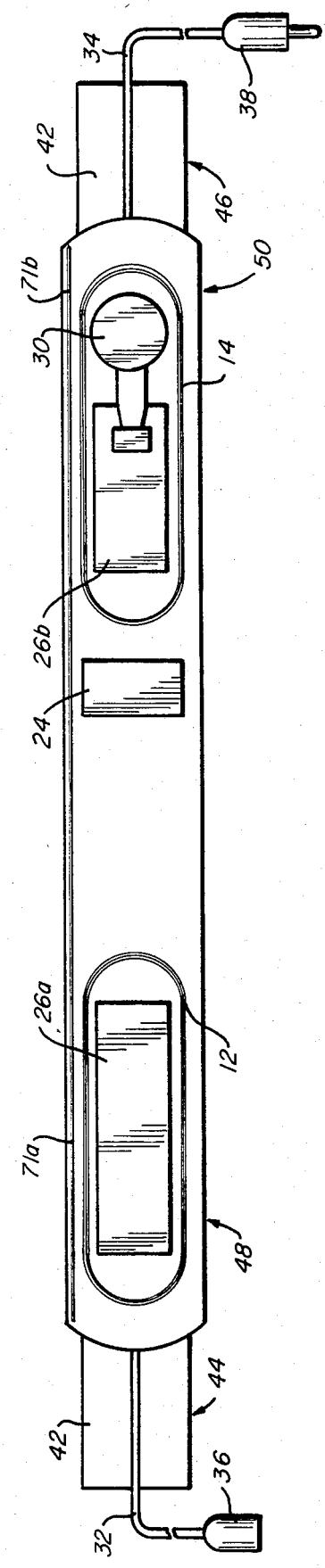
FIG. 4 is an elevation view, taken in cross-section, of a portion of the patient unit of FIG. 3.

Considering the patient unit P (FIGS. 1, 3 and 4) more in detail, a transducer 10 in the form of a plurality of inductive coils or loops 12 and 14 is contained within a belt or vest 16 which mounts the coils 12 and 14 with the thorax or chest of the patient. As the patient's chest moves during breathing, the inductance of the coils 12 and 14 changes with respect to each other. A transmitter 18 (FIG. 1) of the patient unit P forms a radio signal according to the changes in the inductance of the coils 12 and 14 which is transmitted to the central monitor unit C for monitoring and observation.

Figure 5:
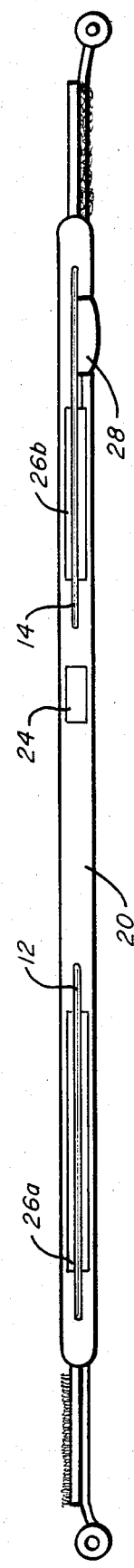
FIG. 5 is a top view of the subject matter of FIG. 4.

In the belt unit 16 (FIGS. 4 and 5) the coils 12 and 14 are mounted spaced from each other within an envelope 20 of a suitable elastomeric material. The envelope 20 is adapted to be inserted through a suitable closable opening in belt unit 16. The envelope 20 has a pouch or pocket 22 formed therewith to receive a battery 24, a set of pockets 26a and 26b to receive electronic circuitry of the patient unit P (FIG. 1), and a pocket 28 (FIGS. 4 and 5) to receive an acoustic transducer or microphone 30 for monitoring cardiac activity of the patient. Electrical conductors 32 and 34 and plugs or jacks 36 and 38 are provided with the envelope 20. Until the plugs 36 and 38 are connected to each other, the battery 24 of the patient unit P does not furnish operating electrical power to the electronic circuitry. However, when the belt unit 16 is mounted on the patient, plugs 36 and 38 are connected to furnish operating electrical power to the electrical circuitry within the belt unit 16.

The envelope 20 of the belt unit 16 is inserted into and mounted within an outer protective cover 40 of a suitable size based on the body dimensions of the patient. Suitable fasteners such as closure straps of nylon tape sold under the trademark "Velcro" of Velcro Corp. 42 are provided on each of end portions 44 and 46 of the belt unit 16 so that the belt unit 16 may be mounted with the chest or thorax of the patient.

The coils 12 and 14 of the transducer 10 are in the form of multi-turn inductors mounted within opposite side portions 48 and 50 of the envelope 20, so that as the patient's chest moves on breathing, the coils 12 and 14 move with respect to each other, causing a change in the mutual or relative inductance of these coils. The coils 12 and 14 are connected to a loop oscillator 52 (FIGS. 1 and 6) in the patient unit P. The oscillator 52 forms an output signal on conductor 52a whose frequency changes based on changes in the inductance of the coils 12 and 14 due to movement of the chest of the patient on breathing.

The output signals from the oscillator 52 are furnished to a phase detector 54 of a phase-locked loop/voltage controlled oscillator circuit 56 (FIGS. 1 and 7). The phase detector 54 detects changes in the frequency of signals from the oscillator 52 and forms an output signal through an impedance network 58 and integrator 60 over conductor 56a to threshold detector 62.

In the impedance network 58, capacitor 58a establishes the center tracking frequency for the voltage controlled oscillator portion of oscillator 56, while resistors 58b and 58c establish upper and lower operating frequency limits for oscillator 56. Resistor 58d and capacitor 58e establish the response time, or the rate at which tracking is performed, by oscillator 56. Finally, a loop resistor 58f in conjunction with integrator 60 establishes a threshold level for the signal formed for tracking in the phase locked loop/voltage controlled oscillator 56.

Figure 8:
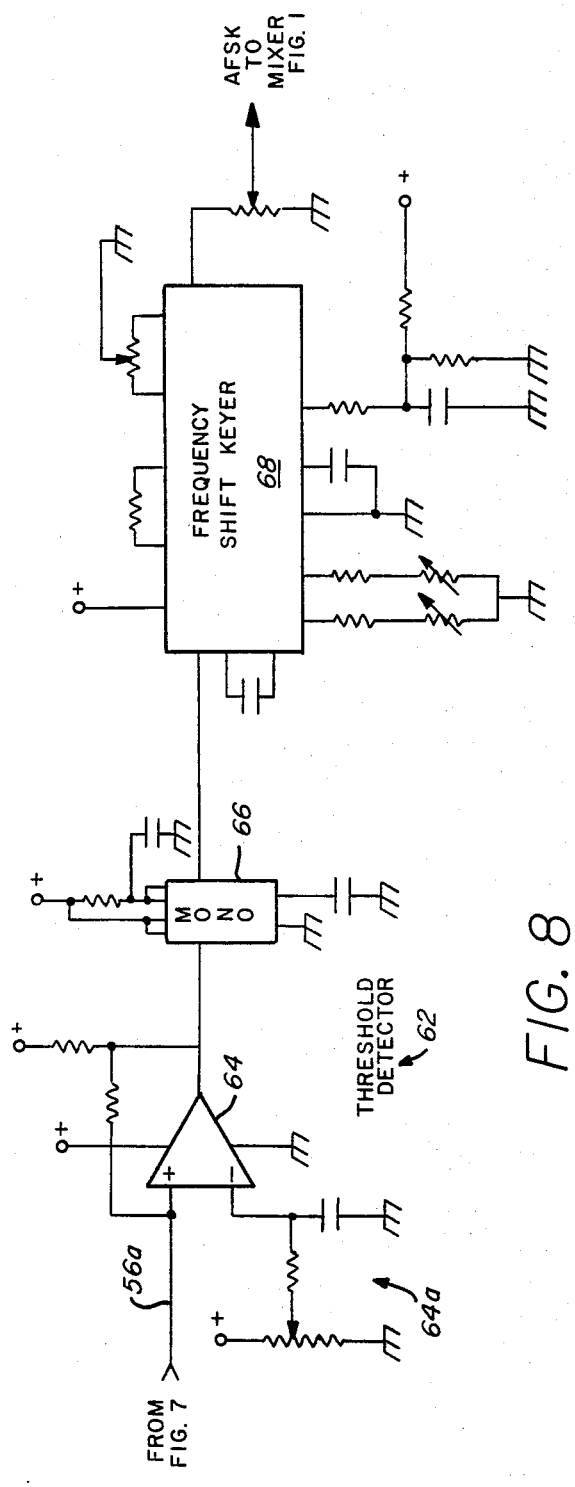

Integrator 60 functions to form a self-adjusting threshold voltage level based on quiescent condition readings when the patient unit P is first attached to the patient. The impedance values of components of the integrator 60 are such that within ten or twenty seconds after attaching the patient unit P to the patient, a threshold voltage level based on the particular patient is established. Thus, with integrator 60, automatic calibration for the particular patient is achieved, permitting adaptation of patient unit P for use with patients having different breathing rates and physical sizes. Further, no electronic circuit changes such as changing impedance values or adjusting potentiometer settings are required to perform this adaptation. Signals formed in the oscillator 56 and integrator 60 are furnished over conductor 56a to a comparator 64 (FIG. 8) of the threshhold detector circuit 62 which detects level changes, due to breathing movements of the patient, in the signals formed in the oscillator 56. A resistor-capacitor network 64a is connected to function as a positive input of the comparator 64 to furnish a reference level signal for comparison with the signal from integrator 60 on conductor 56a. When a level change is detected in the comparator 62 indicating a breath being taken by the patient, a monostable multivibrator 66 is activated to form an output pulse train. The signal formed in the frequency shift key circuit 68 is provided to a mixer circuit 70 and therefrom the very high frequency (VHF) frequency modulation transmitter 18 for transmission by antenna 71 having dipoles 71a and 71b (FIG. 4) to the central unit C for monitoring.

Figure 10:
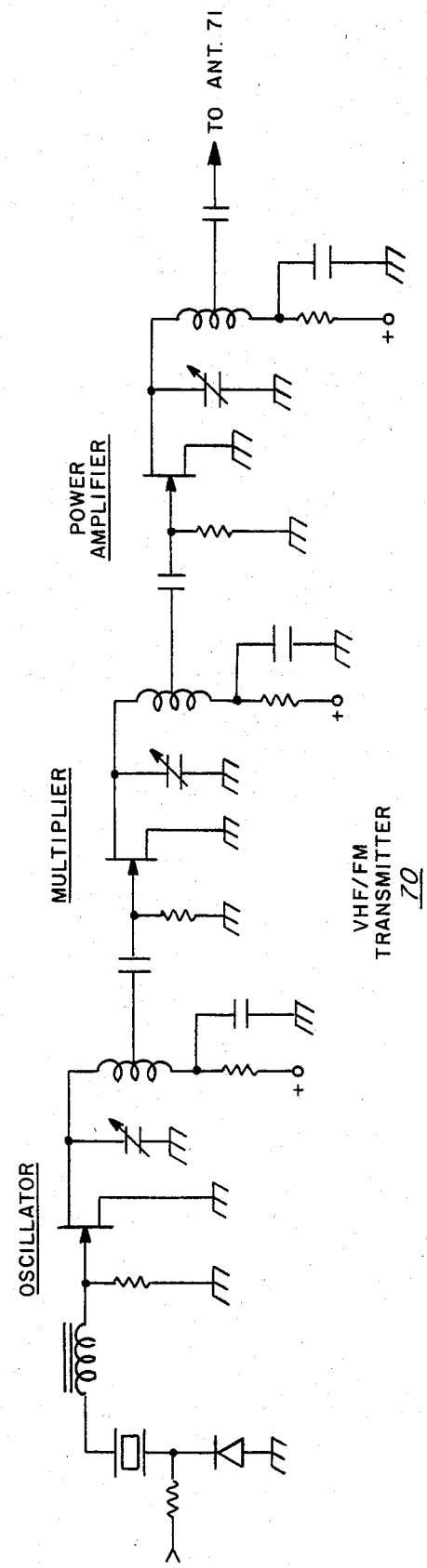

The microphone 30 of the cardiac monitor portion of the patient unit P is electrically connected to a low frequency amplifier circuit 72 (FIGS. 1 and 9) which includes an amplifier 74 (FIG. 9) and an amplifier 76 serving as a two-stage active direct current filter. The output signal from the amplifier 76 is furnished to threshold detector 73 and formed on each heartbeat of the patient. Pulses formed in amplifier 72 and passed by threshold detector 73 (FIG. 10) are applied to a keyed oscillator 75 whose output is applied to linear mixer 70.

Signals so furnished to the mixer 70 representing cardiac activity, are ready for transmission by the transmitter 18 to the control central unit C for observation and monitoring. The patient unit P thus forms a vital signs signal comprised of a respiratory portion sensed by coils 10 and 12 and a cardiac portion sensed by transducer 30, which are sent to the central unit C.

The central unit C of the present invention may take the form of a single channel unit, of the type shown in FIGS. 11-17, for home use for a single infant or other patient, or a multi-channel unit for use with a plurality of patients in locations such as a maternity ward or hospital intensive care or emergency room. In the latter situation, each of the patient units P is uniquely indentified by a suitable indentifier such as: a particular address code modulated onto the vital sign signal transmitted by the transmitter 70 as a part of the radio signal; an assigned frequency channel in a frequency-division multiplexing system; or an assigned time slot in a time-division multiplexing system. After identification the vital signs signal for each particular patient would be processed in the manner of the single channel unit and displayed, either periodically or on a multiple display panel with a display assigned to each patient being monitored.

In the control unit C, radioed vital signs signals from each of the patient units P are received and processed in a VHF frequency modulation receiver 82. Received vital sign signals for each patient, after decoding to identify the patient in multi-channel units, or with no decoding for single channel units, are passed from the receiver 82 furnished through a frequency setting impedance network 84 (FIG. 11) and an amplifier 86 of a wide band amplifier 88 to a carrier detector amplifier 90, a high filter amplifier 92 and a low filter amplifier 94.

In the presence of the carrier signal from the receiver 82, the detector amplifier 90 furnishes an output signal to a monostable multivibrator 96 (FIG. 14) functioning as a pulse stretcher. The lengthened pulses from multivibrator 96 cause an indicator photodiode 98 of a display D to indicate at a suitable frequency the presence of the carrier signal and thus telemetry from the patient unit P. For example, pulse stretcher 96 may form pulses of a length such that diode 98 is substantially constantly energized in the presence of telemetry from patient unit P. In the absence of such a carrier signal, an alarm photodiode 100 is illuminated by the pulse stretcher 96 so that appropriate action may be taken.

Figures 12, 13:
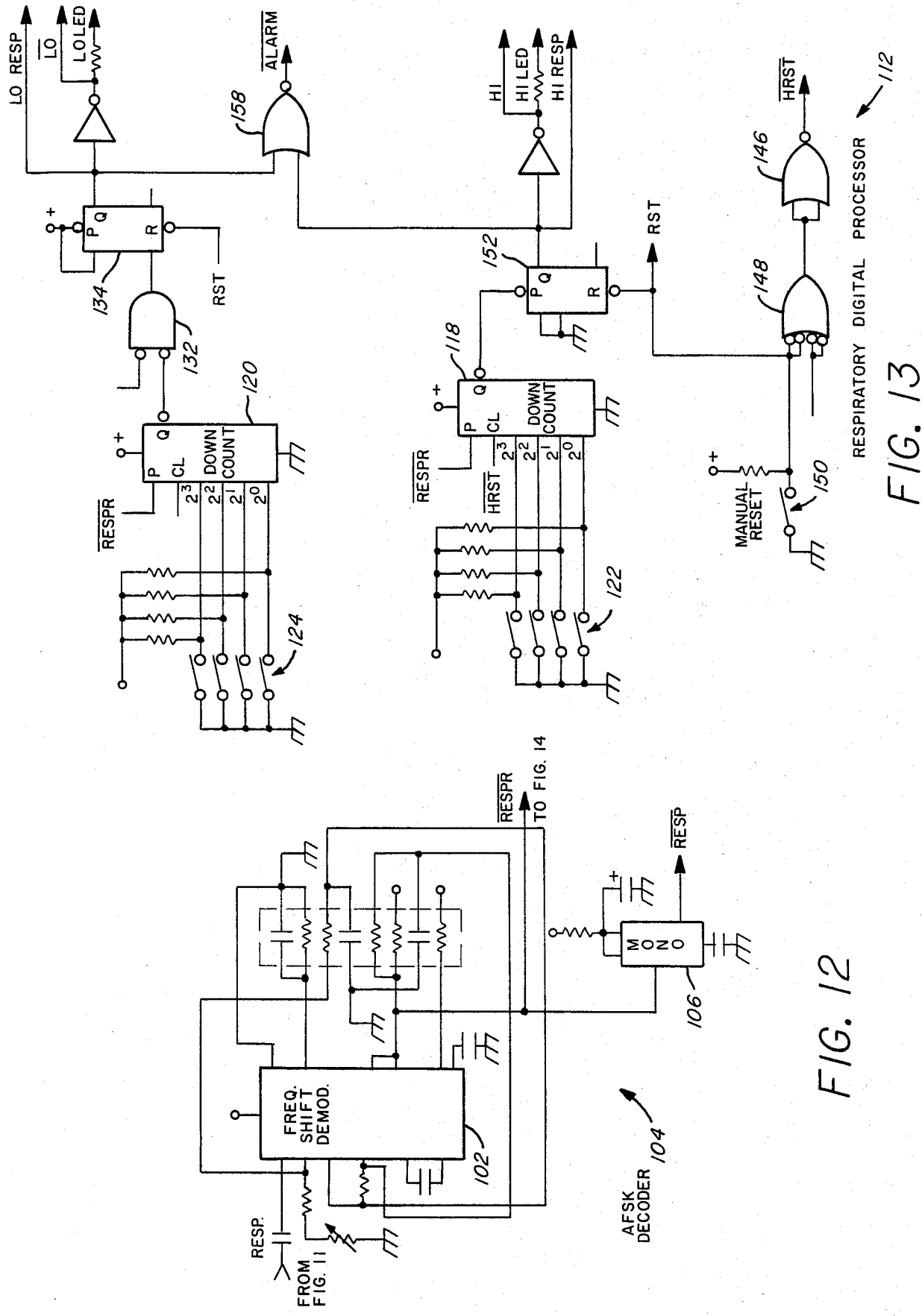

The high filter amplifier 92 (FIG. 11) functions in conjunction with network 84 as a high pass filter amplifier and furnishes respiratory portions of the incoming vital sign signal from the patient unit P to a phase locked loop demodulator 102 (FIG. 12).

The phase locked loop shift demodulator 102 activates a monostable multivibrator 106 causing a pulse to be formed when respiration is indicated by the respiratory portion of the signal received from the patient unit P. The monostable multivibrator 106 forms an output pulse each time an indication of respiratory activity is transmitted from the patient unit P to the central unit C. Output pulses from the multivibrator 106 are furnished to a pulse stretcher of display unit D (FIG. 14), causing an indicator photodiode 110 to indicate the presence of a respiratory activity in the patient being monitored. The period or time duration of the pulses formed in the monostable pulse stretcher 108 may be substantially equal in duration to the time interval between breaths. In this manner, so long as respiratory signals are being received at a normal rate in the central unit C, the photodiode 110 is energized to indicate the receipt of such signals.

The phase locked loop demodulator 102 further furnishes an output signal indicative of the status of respiratory activity of the patient to a digital processor circuit 112 (FIG. 13) for further processing.

In the respiratory digital processor 112 (FIG. 13), the respiration signal detected in the phase locked loop circuit 104 is furnished to each of a high respiration rate counter 118 and a low respiration rate counter 120. The high rate counter 118 has an established acceptable upper limit for the respiration rate of the particular patient established and provided thereto by an input mechanism such as limit setting binary coded decimal switches 122. Similarly, the low rate respiratory counter circuit 120 has an established acceptable lower breathing rate limit furnished thereto by an input mechanism in the form of limit setting binary coded decimal switches 124.

Figure 2:
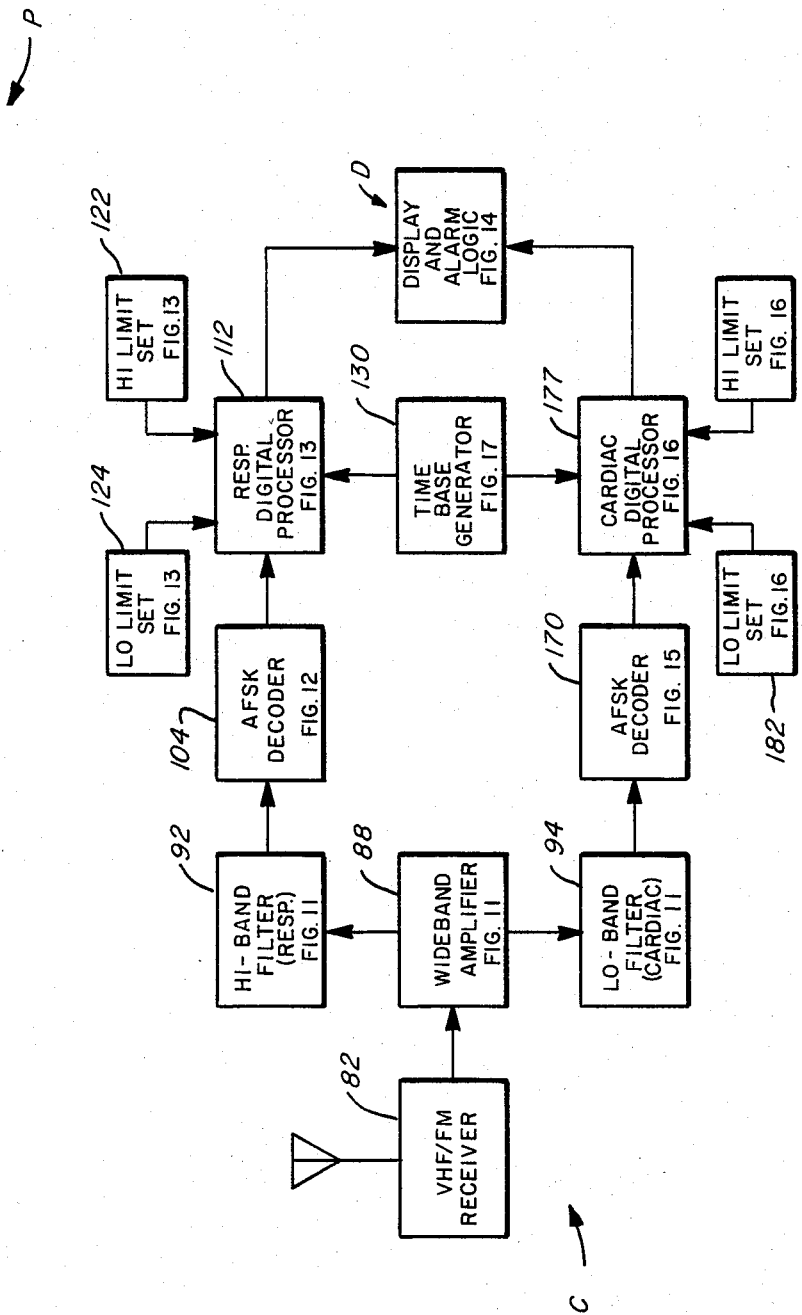
FIG. 2 is a schematic electrical circuit diagram of a central unit according to the present invention.

Turning first to the low rate counter 120 which senses apnea of the patient, counter 120 is preset and loaded with the count established by the switches 124 at the occurrence of each pulse furnished thereto from the phase lock loop demodulator circuit 104. The counter 120 decrements the count furnished thereto by the switches 124 each time a clock signal occurring at a frequency $\phi_1$ is provided thereto from a time base generation clock circuit 130 (FIGS. 2 and 17).

The counter 120 (FIG. 13) thus is periodically reset by the output signal from the FSK decoder each time a respiration portion of the vital sign signal is received from the patient unit P. In the event that a predetermined count number established by the switches 124 is achieved in the counter 120 before a respiration signal is provided thereto from the decoder 104, indicating apnea for a predetermined time interval, a Q output of the counter 120 changes state. On the next occurrence of a clock signal $\phi_3$ from clock 130, this change is transmitted through a gate 132 to a low respiration flip-flop 134, which then changes state to a "low respiration" state. The output of the flip-flop 134 is connected through an inverter 136 of display D (FIG. 14) to energize a low respiration alarm photodiode 138 indicating that a low respiration rate is currently being sensed by the patient unit P. In this event, someone is alerted to investigate the matter and take action.

The high respiration counter 118, like the counter 120, is a programmable down counter receiving a predetermined count level established by the setting of switches 122 each time a respiration pulse is furnished thereto from the decoder 104. The counter 118 is reset by a high reset pulse furnished thereto through gates 146 and 148 at a frequency $\phi_2$ from clock 130. A high reset pulse is also formed in gates 146 and 148 when a manual reset switch 150 is closed. In the event that the counter 118 reaches the upper count limit established by the switches 122 before a high reset pulse is furnished thereto through the gates 146 and 148, a high respiration flip-flop 152 is caused to change state activating an alarm photodiode 154 through an inverter 156 (FIG. 14) to indicate a "high respiration" state. As a further and additional alarm in addition to diodes 138 and 154 to indicate abnormal respiratory rate, each of the respiration state flip-flops 134 and 152 are connected through a NOR gate 158 to activate a suitable alarm in the event that an abnormal high or low respiratory rate is being detected from the radio signal sent from the patient unit P.

In the clock 130 (FIG. 17) the clock signals $\phi_1$, $\phi_2$, and $\phi_3$ discussed above in connection with the respiratory rate processor circuit 112, as well as an additional clock pulse at a frequency phase $\phi_4$ are formed. In the oscillator circuit 130, a reference oscillator circuit 162 operating, for example, at a frequency of 16.384 kilohertz furnishes clock signals at this frequency to a multistage binary counter 164. The binary counter 164 counts the pulses furnished thereto and provides the output clock signal $\phi_1$ with pulses occurring at the rate of one per second, the output clock signal $\phi_3$ occurring at a rate of four kilohertz and another output clock signal $\phi_4$ with pulses occurring every one-hundred twenty-five milliseconds or at a rate of eight pulses per second. The clock signal $\phi_1$ formed in the counter 164 is further provided to a binary counter 166 which forms an output pulse in response to a count of sixteen pulses at the frequency $\phi_1$ being furnished thereto. When the count of sixteen is reached, the output clock frequency $\phi_2$ is furnished through a NAND gate 168 at a rate of one pulse per sixteen seconds.

In the central unit C, an phase locked loop demodulator circuit 170 (FIGS. 2 and 15) receives cardiac portions of the vital sign signals provided through the high filter amplifier 94. The decoder circuit 170 includes a demodulator 171 which forms output signals indicative of cardiac activity received by radio transmission from the patient unit P. Demodulator 171 forms, in conjunction with a filter network 172, cardiac signals which are furnished to a low cardiac counter 174 and high cardiac counter 176 (FIG. 16) of a cardiac digital processor 177. The cardiac signals from the decoder 170 are further furnished to a cardiac indicator pulse stretcher monostable multivibrator 178 (FIG. 14) which drives a cardiac indicator photodiode 180 to indicate the receipt of cardiac signals from the patient unit P. As with pulse stretcher 108, pulse stretcher 178 may be set to form pulses at a rate substantially equal to the time interval between normal conditions, in this case heartbeats, so that diode 180 remains on, during regular or normal situations, substantially all the time.

The low cardiac counter 174 receives a predetermined count represented by the setting of binary coded decimal switches 182 each time a cardiac pulse signal is formed in the decoder 170. The counter 174 is decreased in count at the clock rate $\phi_4$ or eight pulses per second presented thereto over the clock input. So long as cardiac pulses are received in the counter 174 from the decoder 170 at a rate greater than the count set by the switches 182, the counter 174 forms no output signal. Should, however, the time interval set by the switches 182 elapse between receipt of successive cardiac signals, the counter 174 changes state and through a NAND gate 184 causes a low cardiac flip-flop 186 to change state. Low cardiac flip-flop 186 thus forms an output signal which is furnished through an inverter 188 (FIG. 14) to activate a low cardiac rate alarm photodiode 190.

Figure 14:
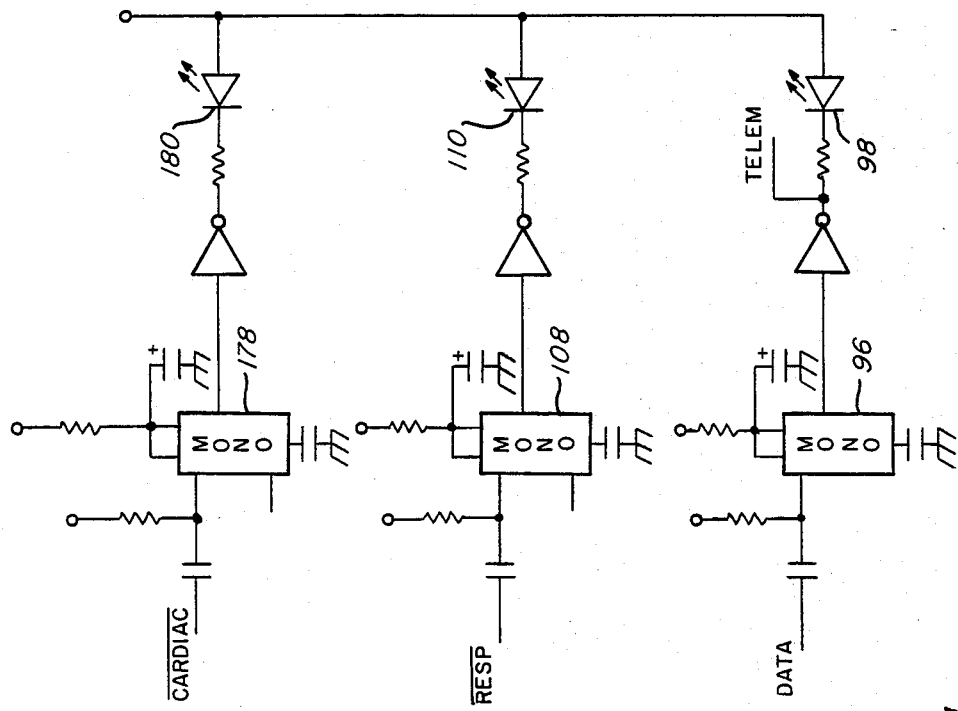
Figure 14:
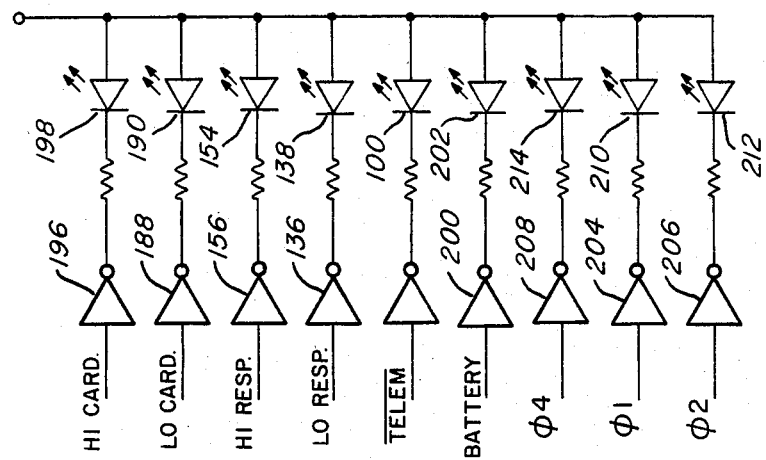
Figures 15, 16:
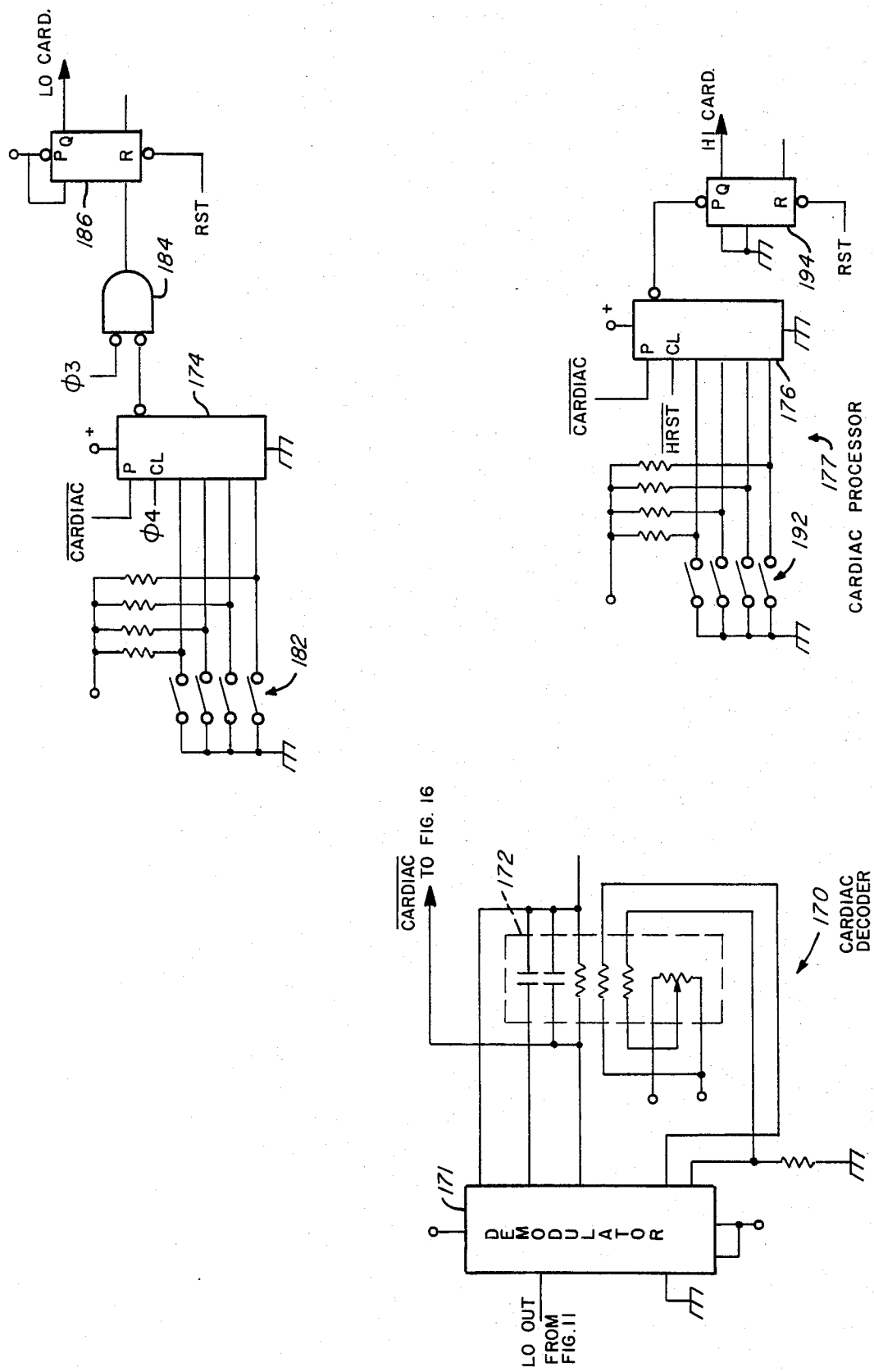

Similarly, the high cardiac counter 176 (FIG. 16) receives a predetermined count number from switches 192 representing an acceptable high cardiac rate. As with the counter 174, the counter 176 is reset in response to receipt of each cardiac pulse from the decoder 170. Should the time between receipt of successive cardiac pulses exceed that established by either the $\phi_2$ signal or the manual reset signal formed in the gates 146 and 148 (FIG. 13), however, the output of the counter 176 changes state, causing a Q output of a high cardiac flip-flop 194 to change state. Flip-flop 194 activates, through an inverter 196, a high cardiac rate alarm photodiode 198 (FIG. 14).

In the processors 112 and 177, the respiratory flip-flops 134 and 152 and the cardiac flip-flops 186 and 194 are each reset at their respective reset input terminals in the presence of an electrical ground formed on closure of the manual reset switch 150. In the display unit, the voltage supply for the central sensor unit C is furnished through an inverter 200 to activate a battery alarm photodiode 202 in the event that the power supplied by the battery goes below an established limit of safety. Similarly, clock pulses $\phi_1$, $\phi_2$ and $\phi_4$ are furnished through inverters 204, 206 and 208 respectively to energize clock monitor photodiodes 210, 212 and 214, respectively, indicating that clock pulses are periodically being formed at the requisite frequencies.

In the operation of the present invention, each patient to be monitored is fitted with a belt or vest 16 containing the inductive coils 12 and 14 and the cardiac monitoring transducer 30. The transducers in the patient unit P detect respiration and cardiac activity in the patient, transmitting radio vital sign signals of respiratory and cardiac activity of the patient through the transmitter 18 to the central unit C. At the central unit C the status of each patient may then be monitored and in the event an abnormal condition is detected, appropriate action may be taken.

The foregoing disclosure and description of the invention are illustrative and explanatory thereof, and various changes in the size, shape, materials, components, circuit elements, wiring connections and contacts, as well as in the details of the illustrated circuitry and construction may be made without departing from the spirit of the invention.

We claim:

1. Apparatus for monitoring vital signs in patients, comprising:
   (a) transducer means for detecting vital signs of such a patient, said transducer means comprising first and second inductive coil means wherein each coil means comprises a coil whose core area remains constant in size;
   (b) means for mounting said transducer means relative to the patient's thorax whereby said first and second coil means are mounted spaced from each other so that, as the patient's thorax moves on breathing, said first and second coil means move with respect to each other to change the mutual inductance of said first and second coil means in response thereto; and
   (c) transmitter means for forming a radio signal which changes according to changes in the mutual inductance of said first and second coil means due to relative movement of said first and second coil means reflecting changes in the patient's breathing.

2. The apparatus of claim 1, wherein said transmitter means comprises encoder means forming a burst frequency modulated signal on detection of breathing.

3. The apparatus of claim 1, wherein said transmitter means is mounted in said means for mounting.

4. The apparatus of claim 1, further including power supply means mounted in said means for mounting for providing operating power to said transducer means and said transmitter means.

5. The apparatus of claim 1, wherein said means for mounting comprises a belt adapted to be mounted about the patient's thorax.

6. The apparatus of claim 1, further including oscillator means forming an output signal whose frequency changes based on changes in mutual inductance of said inductive coil means.

7. The apparatus of claim 6, further including phase-locked loop means forming a signal whose output changes according to changes in the frequency of the output signal of said oscillator means.

8. The apparatus of claim 7, further including detector means for detecting level changes in the signal formed in said phase-locked loop means.

9. The apparatus of claim 8, wherein said transmitter means forms a different radio signal in response to detection of a level change by said detector means.

10. The apparatus of claim 1, further including cardiac monitor means mounted in said means for mounting for monitoring cardiac activity of the patient.

11. The apparatus of claim 10, wherein said transmitter means further comprises means for transmitting a radio signal indicating cardiac activity of the patient.

12. The apparatus of claim 10, wherein said cardiac monitor means comprises acoustic transducer means forming pulses in response to the patient's heartbeats.

13. The apparatus of claim 12, wherein said transmitter means comprises encoder means forming a frequency shift keyed signal on detection of breathing.

14. The apparatus of claim 13, further including mixer means for mixing the pulses formed in said acoustic transducer means with the frequency shift keyed signal of said encoder means.

15. The apparatus of claim 1 as part of a system for monitoring vital signs in one or more patients comprising:
   (a) a plurality of patient unit means, each said patient unit means being provided for one such patient and comprising such transducer means, mounting means and transmitter means for providing a radio signal which reflects changes in the patient's breathing; and
   (b) central unit means for monitoring the vital signs of the patients, said central unit means comprising:
      (1) receiver means for receiving the radio signal formed in said transmitter means;
      (2) display means for displaying the patient's vital signs as indicated by the radio signals received in said receiver means.

16. The apparatus of claim 15, wherein each patient unit means further comprises cardiac monitor means mounted in said means for mounting for monitoring cardiac activity of the patient.

17. The apparatus of claim 16, wherein each said transmitter means further comprises means for transmitting a radio signal indicating cardiac activity of the patient.

18. The apparatus of claim 16, wherein each said cardiac monitor means comprises acoustic transducer means forming pulses in response to the patient's heart beats.

19. The apparatus of claim 18, wherein each said transmitter means comprises encoder means forming a burst modulated signal on detection of breathing.

20. The apparatus of claim 19, wherein each patient unit means further comprises mixer means for mixing the pulses formed in said acoustic transducer means with the burst modulated signal of said encoder means.

21. The apparatus of claim 15, wherein said plurality of patient unit means are each associated with a different patient and form radio signals according to the patient's vital signs and said receiver means of said central unit means receives signals from said plurality of said transmitter means.

22. The apparatus of claim 15, wherein said receiver means comprises:
filter means for filtering signals representing the patient's vital signs from the received radio signals;
decoder means for decoding each patient's vital signs from the filtered signals;
processor means for processing the decoded signals to determine the patient's vital signs.

23. The apparatus of claim 22, further including limit set means for establishing acceptable limits of each patient's vital signs.

24. The apparatus of claim 23, wherein said processor means comprises means for detecting when a patient's vital signs are not within the acceptable limits established by said limit set means.

25. The apparatus of claim 22, wherein each patient unit means further comprises
(a) cardiac monitor means mounted in said means for mounting for monitoring cardiac activity of the patient;
(b) said transmitter means further comprising means for transmitting a radio signal indicating cardiac activity of the patient;
(c) said cardiac monitor means comprising acoustic transducer means forming pulses in response to the patient's heart beats;
(d) said transmitter means also comprising encoder means forming a frequency shift keyed signal on detection of breathing; and
(e) mixer means for mixing the pulses formed in said acoustic transducer means with the frequency shift keyed signal of said encoder means.

26. The apparatus of claim 25, wherein said filter means comprises:
(a) filter means for filtering respiration signals representing the patient's respiration from the received radio signals; and
(b) filter means for filtering cardiac signals representing the patient's cardiac activity from the received radio signals.

27. The apparatus of claim 26, wherein said decoder means comprises:
(a) means for decoding the filtered respiration signals; and
(b) means for decoding the filtered cardiac signals.

28. The apparatus of claim 27, wherein said processor means comprises:
(a) means for processing the decoded respiration signals; and
(b) means for processing the decoded cardiac signals.

* * * * *